United States Patent [19]

Patel et al.

[11] 4,276,780
[45] Jul. 7, 1981

[54] OPTOACOUSTIC SPECTROSCOPY OF THIN LAYERS

[75] Inventors: Chandra K. N. Patel, Summit, N.J.; Andrew C. Tam, Sunnyvale, Calif.

[73] Assignee: Bell Telephone Laboratories, Incorporated, Murray Hill, N.J.

[21] Appl. No.: 98,630

[22] Filed: Nov. 29, 1979

[51] Int. Cl.$^3$ .................................... G01N 29/00
[52] U.S. Cl. .................................... 73/643
[58] Field of Search .......... 73/643, 579, 655; 331/94.5 R, DIG. 1; 250/343; 356/432

[56] References Cited

U.S. PATENT DOCUMENTS

| | | | |
|---|---|---|---|
| 3,811,782 | 5/1974 | Kerr | 356/432 |
| 4,137,991 | 2/1979 | Melcher et al. | 73/643 |

OTHER PUBLICATIONS

E. L. Kerr; "Alphaphone-Method for Measuring Thin Film Absorption at Labor Wavelengths," *Applied Optics*, vol. 12, No. 10, pp. 2520-2527, Oct. 1973.

F. A. McDonald; "Photoacoustic Determination of Small Optical Absorption Coefficients: Extended Theory," *Applied Optics*, vol. 18, No. 9, pp. 1363-1367, May 1979.

A Hordvik et al.; "Photoacoustic Technique Determining Optical Absorption Coefficients in Solids," *Applied Optics*, vol. 16, No. 1, pp. 101-107, Jan. 1977.

A. Hordvik et al.; "Photoacoustic Measurements of Surface and Bulk Absorption in HG/DF Laser Window Materials," *Applied Optics*, vol. 16, No. 11, pp. 2919-2924, Nov. 1977.

M. M. Farrow et al.; "Piezoelectric Detection of Photoacoustic Signals," *Allied Optics*, vol. 17, No. 7, pp. 1093-1098, Apr. 1978.

R. J. von Gutfeld et al.; "20-MHZ Acoustic Waves From Pulsed Thermoelastic Expansions of Constrained Surfaces," *Applied Physics Letters*, vol. 30, No. 6, pp. 257-259, Mar. 1977.

C. Patel et al.; "Optoacoustic Spectroscopy of Liquids," *Applied Physics Letters*, vol. 34, No. 7, pp. 467-470, Apr. 1979.

C. Patel et al.; "Optical Absorption Coefficients of Water," *Nature*, vol. 280, pp. 302-304, Jul. 1979.

A. Rosenewaig; "Photoacoustic Spectroscopy," Advances in Electronics and Electron Physics, vol. 46, p. 208, 1978.

*Primary Examiner*—Stephen A. Kreitman
*Attorney, Agent, or Firm*—Peter V. D. Wilde

[57] ABSTRACT

Method and apparatus for high-sensitivity optoacoustic (OA) spectroscopy of condensed matter in thin layer form. The layer to be investigated is to be in intimate contact with a solid substrate that is essentially transparent to the probe radiation, and that is capable of transmitting ultrasonic vibrations. Intermittent probe radiation, focused to a diameter typically $10^{-3}-1$ cm when incident on the layer, cause local heating and dimensional change in the irradiated region of the layer. The dimensional change of that region causes deformation of the adjacent substrate material, the irradiated layer region thereby becoming a source of ultrasonic waves that are spreading out in the substrate from the source region, and which can be observed with appropriate detection means at a location remote from the source. The method is applicable to liquids, solids suspended in liquids, gels, continuous or discontinuous solid films, powders, monolayers of strongly absorbing atoms, surfaces, and layerlike distributions of absorbing atoms within an essentially transparent matrix. Possible choices of probe radiation are not only the conventional ones of visible, near-UV, and near-infrared electromagnetic radiation, but also, for instance, X-rays, vacuum UV, and infrared, and matter beams, such as electron, ion, or neutral atom beams. Typical means for detecting the ultrasonic signal are ultrasonic bulk wave or surface wave transducers. For sufficiently short probe pulses, the amplitude of the ultrasonic signal is directly proportional to the absorption of the layer material at the frequency of the probe radiation, but longer pulses, such as, for instance, are obtained from mechanical choppers, can be used also. Apparatus is disclosed that minimizes interference with the measurement due to scattered light and transducer ringing, and that permits the measurement of fractional absorption down to $10^{-6}$ or less.

14 Claims, 7 Drawing Figures

OPTOACOUSTIC SPECTROSCOPY OF THIN LAYERS

BACKGROUND OF THE INVENTION

1. Field of the Invention

This invention is in the field of absorption spectroscopy, more particularly, it pertains to optoacoustic absorption spectroscopy of condensed matter in the form of thin layers.

2. Description of the Prior Art

Conventional optical spectroscopy techniques tend to fall into two major categories, namely, one can study either the optical photons that are transmitted through the material under study, or those that are scattered or reflected from that material. During the past few years, another optical technique has been developed. This technique, called optoacoustic (OA) spectroscopy, is distinguished from the conventional techniques chiefly by the fact that, even though the incident energy is in the form of optical photons, the interaction of these photons with the material under investigation is studied not through subsequent detection and analysis of photons, but rather through measurement of the energy absorbed by the material due to its interaction with the incident beam. One of the principal advantages of OA spectroscopy is that in principle it enables one to obtain spectra, similar to optical absorption spectra, of any type of solid, liquid, or gaseous material. A recent review of the field of OA spectroscopy can be found in the article by Allan Rosencwaig, "Photoacoustic Spectroscopy" in *Advances in Electronics and Electron Physics*, Volumne 46, Academic Press (1978).

The presently used method for OA spectroscopy of thin films is an extension of a method for OA spectroscopy of gases. That latter technique consists of confining the gaseous sample to be measured in an experimental chamber having typically two collinearly arranged parallel optical windows having extremely low absorption at the frequency of the probe radiation, irradiating the sample through these windows with chopped monochromatic light, and measuring the chopping frequency change in gas pressure due to the heating effect of the energy absorbed by the gas sample. The pressure variations are generally measured with a sensitive gas microphone. By filling the experimental chamber with a gas transparent to the probe radiation, and by placing a thin film of the condensed matter to be studied into the radiation path inside the experimental chamber, one can determine the absorption spectrum of the thin film material, since the radiant energy absorbed by the film will increase the temperature of the film, resulting in an increase in the gas pressure inside the experimental chamber in proportion to the energy absorbed. Such apparatus has, for instance, been described in an article by E. L. Kerr, *Applied Optics*, Volume 12, page 2520, (1973). See also U.S. Pat. No. 3,811,782, "Method and Apparatus for Measuring Thin Film Absorption at Laser Wavelengths", E. L. Kerr, May 21, 1974.

The described gas-phase microphone technique for condensed samples has several disadvantages that limit its usefulness. First of all, it relies on the inefficient diffusion of thermal energy from the sample into the gas volume. This makes this technique slow and of low sensitivity, typically useful only if fractional absorption in the film exceeds about 1 percent. Furthermore, effects due to scattered light are troublesome, since such light, when absorbed by the chamber walls, contributes to the pressure increase in the gas due to the resultant heating of the experimental chamber.

A different technique exists for the measurement of optical absorption in bulk samples of condensed matter. In the case of a solid sample a strain transducer, typically a piezoelectric transducer, is placed in direct contact with the sample. A pencil of chopped light, transmitted through the sample, will cause the illuminated volume to expand in direct proportion to the absorption coefficient and the coefficient of thermal expansion of the material. This results in strain waves radiating out from the cylindrical "source" region, and these ultrasonic strain waves can be detected by an appropriately placed transducer. See, for instance, A. Hordvik and H. Schlossberg, *Applied Optics*, Volumne 16, pages 101–107, (1977), where experimental details of the method are given.

OA spectroscopy on bulk liquid samples can be done by using an experimental cell similar in principle to that described for use with gaseous samples, i.e., having collinear parallel transparent entrance and exit windows. Two types of cells have been used. In one the cell body consists essentially of a piezoelectric transducer in the shape of a cylindrical shell, and in the other a piezoelectric transducer is mounted in an appropriate position in a wall of the experimental cell. Typically in both cases thus the transducer is in direct contact with the liquid sample. For an example of the former approach, see, for instance, the article by A. Rosencwaig, cited above, and an example of the latter can be found in an article by C. K. N. Patel and A. C. Tam in *Applied Physics Letters*, Volume 34, pages 467–470, (1979). In both types of cell the piezoelectric transducer detects the elastic waves that are generated in the sample liquid by a mechanism analogous to the one described for bulk solid samples, and thus OA spectroscopy on bulk liquid samples is quite similar to such spectroscopy on bulk solid samples.

Prior art bulk techniques that use chopped probe radiation allow the measurement of absorption coefficients in the $10^{-4}$ to $10^{-5}$ cm$^{-1}$ range, using light beams of a few hundred mW power. The sensitivity limit of the method is typically determined by thermal interaction of the transducer with scattered radiation. The use of chopped light typically also leads to problems due to heat diffusion because of the relatively long pulse length of chopped light, which makes the prior art techniques essentially optothermal rather than optoacoustic. Furthermore, since typically measurement cells for bulk liquid samples are not disposable, the possibility of unwanted contamination of the sample exists in prior art techniques.

SUMMARY OF THE INVENTION

Our invention involves a method and apparatus for high sensitivity OA spectroscopy of thin layers of condensed matter. It is not only applicable to continuous liquid or solid films but also to powders, gels, suspensions of solid particles in liquids, and even to layers of absorbing atoms or molecules within a relatively nonabsorbing solid matrix. Furthermore, the sample layer could even be a surface layer of the substrate that is relatively more absorbing than the bulk of the substrate due to some physical or chemical change within the surface layer. By "layer" we henceforth mean any essentially two-dimensional distribution of condensed matter in intimate contact with an appropriate substrate.

By "intimate contact" we mean contact that results in some strain in the substrate in response to energy absorbed from intermittent probe radiation by the sample layer. The method is useful not only with conventional probe beams, i.e. electromagnetic radiation in the visible, near-UV, or near-infrared part of the spectrum, but also with X-ray or vacuum UV (VUV) beams, as well as with matter beams such as electron, ion or neutral atom beams, and the term "probe radiation" is meant to include all of these as well as other probe beams that may later be found to be compatible with our method. Because of the so-called deBroglie relation, i.e., $E=h\nu$, with h Planck's constant, and $\nu$ the frequency associated with a material particle of energy E, one can assign a frequency to matter beams, and we will henceforth speak of the frequency of the probe radiation without distinguishing between electromagnetic radiation or particles. Due to the high sensitivity of our method, only minute quantities of the absorbing material are required to yield a detectable signal, thus it is for instance possible to carry out absorption spectroscopy on monolayers of sufficiently absorbing atoms. The method can be made to be truly optoacoustic in that it can eliminate all influences due to thermal diffusion that have plagued prior methods.

In order to practice our invention one typically prepares a layer of the material to be studied, that is of the order of several microns thick, although much thinner layers, down to monolayers, as well as thicker layers, can be studied. The substrate supporting the layer is to be essentially transparent to the probe beam used. "Essentially transparent" is used herein in an operative sense, namely, it implies that any absorption of the probe pulse in the substrate is small enough so as not to interfere unduly with the OA measurement of the absorption in the sample layer. For instance, fused quartz is an excellent substrate material for spectroscopy in the visible and the adjacent UV region that fulfills this requirement. For ease of exposition we will henceforth describe the invention in terms appropiate to optical spectroscopy, but it will be understood that this is not intended to limit the scope of our disclosure.

Irradiating a small region of the layer with short light pulses as, for instance, from a pulsed laser, results in a localized temperature increase in the layer material due to the absorption of radiant energy from the light pulse. This temperature rise is accompanied by a change of the linear dimensions of the irradiated layer material, due to the usual thermal expansion. This change of dimensions results in a deformation of the adjacent portion of the substrate, resulting in the generation of elastic waves traveling away from this source region. We will refer to these irradiated regions as the "layer source region" and the "substrate source region," respectively. The elastic waves can be detected, typically by the use of a piezoelectric transducer. We will refer to that part of the substrate where detection takes place as the "detection region." The waves generated are typically compressional waves and shear waves, as well as surface acoustic waves, for all of which quartz has very small absorption coefficients, of the order of $10^{-3}$ cm$^{-1}$ at a frequency of 1 MHz. A detector can thus be placed at considerable distance from the source region, of the order of 10 cm, and still detect the essentially unattenuated ultrasonic waves generated by the probe pulse. We will refer to all of these strain waves generated in the substrate as "ultrasonic waves." If the light pulse is short compared to the time required for thermal diffusion over a distance of the order of the radius of the irradiated region then the amplitude of the ultrasonic signal is directly proportional to, inter alia, the absorption coefficient of the layer material. The amplitude of some appropriate feature of the output of the detector, typically the amplitude of the first peak that is due to optical absorption in the layer, is thus proportional to the absorption coefficient of the layer material at the frequency of the probe radiation. With appropriate calibration absolute measurements of the absorption coefficient can be obtained.

Our method thus makes possible absorption spectroscopy of very thin layers of material or moderate to high absorptively. It can be applied to layers having a fractional absorption as low as $10^{-6}$, or even less, and thus improves the sensitivity of OA measurements of thin layers by many orders of magnitude. The extension of the method to other than optical probes is possible and depends only on the availability of appropriate substrates. The method is easy to practice, requires no special instrumentation, permits the use of well-known low-noise AC detection techniques, and permits the easy extension of absorption measurements to either low or high temperatures, and allows such measurements in the presence of magnetic or electric fields, radiation, or the like.

BRIEF DESCRIPTION OF THE DRAWINGS/P

FIG. 1 schematically shows an experimental apparatus for OA spectroscopy of a thin liquid film;

FIG. 2 schematically shows a possible substrate geometry that minimizes measurement effects due to scattered light;

DETAILED DESCRIPTION

Figure 1:
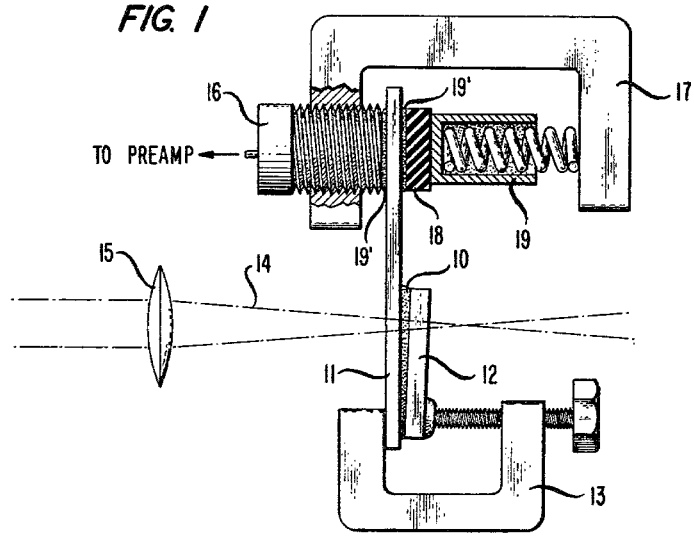

Before giving a detailed description of the application of our method, we want to give some indication of its breadth. As had been pointed out above, the basic requirements of our method are the existence of a substrate that is essentially transparent for the probe radiation, with the substrate permitting the propagation and detection of mechanical waves excited in the substrate by the temperature rise in the layer source region, caused by the absorption of energy from the probe pulse in that region. It is thus the availability of appropriate substrates that primarily determines the breadth of applicability of our method. For instance, the nature of the substrate clearly determines the nature of possible probes. For electromagnetic radiation in the visible and near-UV part of the spectrum fused quartz is a nearly ideal substrate material. The useful range of quartz can be extended into the near infrared, provided certain impurities, such as OH and heavy metal oxides are reduced. In the VUV part of the spectrum appropriate substrate materials are lithium fluoride, calcium fluoride, and the like. For even shorter wavelengths, in the X-ray region, beryllium and carbon are desirable substrate materials, although other materials of low electron density might also be useful. Matter beams, such as electron, ion, or neutral atom beams require substrates that are single crystalline at least in the substrate source region, the crystal oriented to allow channeling of the incident particles through the lattice.

Even though we have so far spoken of the substrate as if it had to be homogeneous, this is clearly not required. It is the substrate source region that has to have low absorptivity, whereas this requirement is nonexistent for any other region of the substrate. This implies that composite substrates are possible, provided that ultrasonic waves can be coupled out of the low-absorption region of the substrate and into the adjacent volume of the substrate. This permits, for instance, the use of a relatively thin "window" mounted in an aperture of a relatively thicker substrate, the latter consisting perhaps of fused quartz because of its desirable ultrasonic properties. Another type of composite substrate structure is a layer structure, consisting of a rigidity-giving "passive" layer and a thin "active" layer involved in the propagation of ultrasonic surface waves. Such an arrangement might be advantageous if a substantial fraction of the acoustical energy coupled into the substrate material propagates in the form of ultrasonic surface acoustic waves. In such a case, the active layer needs to be only several wavelengths of the appropriate surface waves thick.

Although typically piezoelectric detection of the ultrasonic waves in the substrate is most convenient, other detection schemes, such as, for instance, optical readout, are, of course, possible. Piezoelectric detection can be by means of the usual bulk transducer, in which case the substrate, of course, need not itself be piezoelectric. On the other hand, if an appreciable part of the total acoustical energy is in the form of ultrasonic surface waves, then a surface acoustic wave transducer might be advantageously used. Such transducers are typically of the interdigitated kind, deposited directly onto the substrate material. In this case, of course, at least the part of the "active" layer that is within the detection region has to consist of an appropriate piezoelectric material.

We will next give a brief description of some theoretical results that have been derived for the case of optical absorption. However, analogous results apply to other probe beams. It has been shown that both for the cases of surface absorption and of relatively weak bulk absorption of pulsed electromagnetic radiation the following expression applies:

$$(P_o/E_o) = (K\beta\alpha/C_p\rho) \quad (1)$$

where $P_O$ is the acoustic pressure amplitude developed, $E_O$ is the electromagnetic energy in a pulse, K is a constant dependent on the apparatus, $\beta$ is the thermal expansion coefficient, $C_p$ is the specific heat at constant pressure, and $\rho$ is the density of the layer material, and $\alpha$ is the optical absorption coefficient of the layer material for the probe radiation of frequency $\nu$. This expression says that the acoustic pressure developed, when normalized by the energy in the exciting pulse, is proportional to the fraction of pulse energy absorbed from the pulse per unit layer thickness, inversely proportional to the temperature rise produced by this absorbed energy, and directly proportional to the dimensional change resulting from a unit temperature change in the material.

The solution of the theoretical problem is greatly simplified, and the experimental results can be made unambiguous, if the light pulses used are of duration short compared to the time required for thermal diffusion over a distance of the order of the radius of the layer source region, since in this case, the so-called "adiabatic" approximation, one can neglect diffusion of thermal energy out of that region. As is well known, the diffusion length $\lambda_{diff}$ in a time interval $\tau$ is given by the expression:

$$\lambda_{diff} = (4\tau D)^{\frac{1}{2}} \quad (2)$$

where D is the thermal diffusivity. Since for instance D is $\sim 10^{-3}$ cm$^2$ sec$^{-1}$ for most liquids one sees that $\lambda_{diff}$ is $\sim 10^{-4}$ cm, for a pulse length $\tau = 10^{-6}$ sec. Thus the adiabatic approximation can safely be used for source regions of diameter $10^{-3}$ to 1 cm, if such short pulses are used. However, the method disclosed here is not restricted to application in the adiabatic regime and longer pulses can, of course, be used, and we mean by "intermittent radiation" both pulsed as well as chopped or otherwise interrupted probe radiation, regardless of pulse length. As is well known, pulse length can be defined in a variety of ways. For the sake of definiteness, we intend herein "pulse length" to mean the time during which the pulse has amplitude greater than 50 percent of its maximum amplitude.

Theory predicts that for a bulk sample in the adiabatic regime, the acoustic response of the medium to a Gaussian pulse is a compression pulse reaching maximum amplitude slightly before the probe pulse reaches its maximum, followed by a rarefaction pulse of nearly equal amplitude, with the time interval between compression and rarefaction maxima being approximately the probe pulse width. This implies that a piezoelectric transducer, located a distance R from the source region, will register a compression pulse a time (R/$v_c$) after the light pulse, where $v_c$ is the velocity of compression waves in the medium. Similar results apply in the case of a layer, the sample shape of interest in this disclosure. However, since in this case compression waves as well as shear waves and surface waves will be excited in the substrate, a transducer, which typically is sensitive to only one type of wave, detects the appropriate acoustic disturbance with a delay time proportional to the propagation velocity of that type of wave in the substrate.

The constant K of equation (1) can in principle be calculated if one knows the efficiencies of the detectors and the various coupling constants. In practice, however, K will probably be measured experimentally for a given sample by comparing the normalized signals for the sample and that of a layer of known absorptivity. Such calibration procedures are well known and will not be discussed further.

In FIG. 1, we show, in somewhat schematized form, apparatus we used for OA spectroscopy of liquid layers. The same apparatus can of course be used for spectroscopy of solid suspensions in liquid, and, with a trivial and obvious modification, the apparatus could be used for spectroscopy of continuous or discontinuous solid layers. The wedge-shaped layer 10 is confined between substrate 11 and cover plate 12, with one end of the latter clamped by clamping device 13 against the substrate. We show this clamping to be accomplished by a C-clamp but, of course, the desired clamping could be achieved in many different ways. Cover plate 12 merely serves to allow easy thickness determination of the liquid layer, since in such an arrangement this can be accomplished by a mere counting of interference fringes. OA spectroscopy as such does not require confinement of the liquid layer, and the signal observed from an unconfined layer is essentially indistinguishable from that from a confined one. A beam of intermittent electromagnetic radiation 14 is focused by optical system 15 in a manner to result in a source region of the desired size and shape. Typically a circular source region would be desirable, of radius large compared to the thermal diffusion length $\lambda_{diff}$, as given by equation (2). But of course larger source regions could be used, just as pulses longer than the microsecond pulses we have typically used can be employed. It is merely required to take account of resulting non-negligible interference and thermal diffusion effects. Clamping device 17 firmly holds transducer assembly 16 against substrate 11, by means of backing plate 18 and a spring loaded device 19. Plate 18 appropriately consists of rubber or some other rubber-like material. To enhance the coupling of acoustical energy to the transducer and to reduce reflections, very thin layers 19' of a coupling medium, such as, for instance, silicon grease, are placed between substrate and transducer assembly and between substrate and backing plate.

Figure 2:
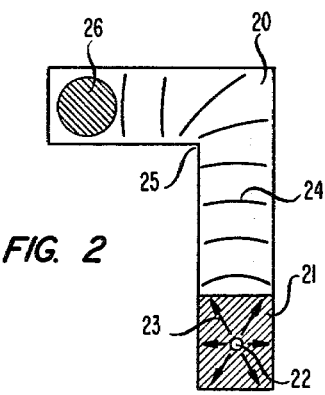

FIG. 2 shows a substrate geometry that we have found effective in reducing the effects of scattered light. The L-shaped substrate 20 is covered on one end with the sample layer, indicated by region 21. The detection region 26 is at the end of the other arm of substrate 20. Layer source region 22 undergoes thermal expansion due to absorption of energy from the probe pulse, as indicated by arrows 23, resulting in the excitation of ultrasonic waves in the substrate, indicated by wave fronts 24 diverging from the substrate source region. Due to diffraction by edge 25 a significant fraction of the acoustical energy radiated by the source region reaches detection region 26. In fact, a substrate, typically having arms 10 cm long and 1 cm wide, and being about 0.1 cm thick, can be thought of as an acoustical waveguide. On the other hand, the small amount of scattered light propagating within the substrate away from the substrate source region will not be diffracted into the transducer arm of the substrate. Instead, the greater part of the light will exit from the substrate and thus will not longer be able to effect the measurement. Of course, FIG. 2 shows only the simplest possible geometry that has the effect of reducing noise due to scattered light, and a variety of other arrangements easily come to mind that would be even more efficient in this respect. For instance, any planar or nonplanar arrangement requiring diffraction around more than one bend would be a possible substrate geometry.

Figure 3:
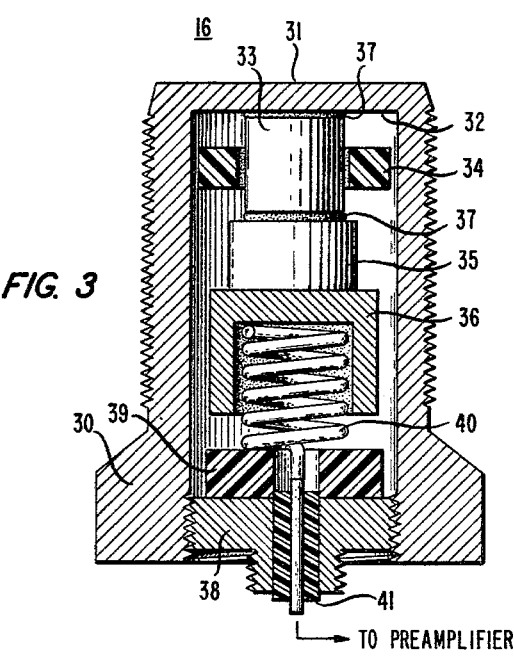
FIG. 3 shows in cross-section a possible transducer assembly.

In FIG. 3 we show the details of a transducer assembly that we have found useful, but of course, many equivalent or similar designs are possible. Housing 30 is fabricated from stainless steel, with the membrane between highly polished surfaces 31 and 32 being about 1 mm thick. Transducer 33 is kept centered by teflon ring 34 and is forced against the membrane by means of spring 40, which is restrained laterally by copper housing 36, to which is soldered lead absorber 35. Very thin layers of grease 37 between membrane surface 32 and transducer 33, as well as between the transducer and the absorber 35, serve to improve acoustical coupling. For clarity's sake, the coupling layers are shown in FIGS. 1 and 3 with greatly exaggerated thickness. Appropriate deformation of the piezoelectric transducer results in the appearance of a voltage between the metalized plane surfaces of the transducer, i.e., the surfaces adjacent to membrane surface 32 and lead absorber 35. Copper bronze spring 40 is in electrical contact with a miniature coaxial connector 38 and thus completes the conductive path between the transducer and the connector, making any electrical signal produced by the transducer available for further processing. Spring 40 pushes against dielectric ring 39, which, together with insulator 41, prevents short-circuiting of the output signal. As can be seen, the transducer assembly forms an essentially complete metallic enclosure, thereby reducing electromagnetic interference with the transducer signal. A further advantage is the relatively large thermal mass of the steel housing 30, which reduces thermal noise due to scattered light that reaches the transducer assembly. Polished surface 31 not only makes good acoustic coupling to the substrate possible but also serves to reflect scattered light incident on it, thereby further reducing thermal noise. Absorber 35 is made of lead because lead has relatively large ultrasonic absorption, thus serving to reduce undesirable effects due to reflected ultrasonic waves. We have used commercially available cylindrical ceramic transducers, poled and dimensioned to respond predominantly to compressional waves of about 1 MHz. However, a wide variety of different materials, shapes, mode dependencies, and resonant frequencies would be equally practical, and any choice would obviously be dictated by the particulars of the measurement planned. For instance, for some applications measurements at much higher or much lower frequencies might be of interest, whereas for other applications it might be desirable to use a broad-band transducer that is responsive to many frequencies. Also, for some applications one might want to detect shear waves, which would require the choice of a transducer responsive to such waves. And, of course, as was indicated above, if surface acoustic waves are of interest then a completely different transducer arrangement would probably be used in place of the transducer assembly shown, namely, an interdigitated surface acoustic wave transducer. In any case, however, the ultrasonic waves detected should be of a frequency much higher than the repetition frequency of the intermittent probe radiation, probably by a factor of about 100 or more.

Figure 4:
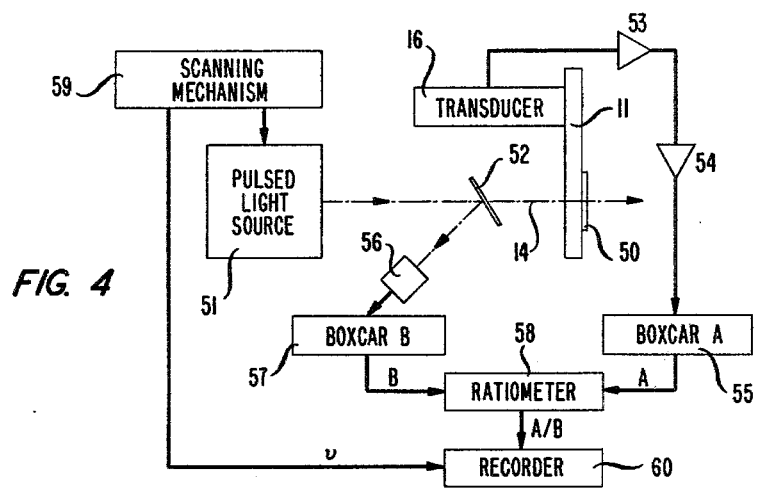
FIG. 4 shows in block diagram form a possible instrumentation scheme for OA spectroscopy of thin layers.

FIG. 4 shows in block diagram form a possible instrumentation scheme for OA spectroscopy of layer material. Pulsed light source 51, typically a pulsed dye laser, emits light pulses at a rate that is controlled in some appropriate manner, and of a frequency determined by scanning mechanism 59. Beam splitter 52 deflects a small fraction of the total intensity, typically 5 percent, onto pyroelectric detector 56. Probe pulse 14 is shown to pass through transparent substrate 11, for instance, a fused quartz slide, and then through layer 50 that is in intimate contact with the substrate. The output of transducer 16 is fed to low-noise bandpass preamplifier 53. Because of the high electrical impedance of most piezoelectric transducers a relatively high-quality preamplifier, having high input impedance and low noise figure, physically in close proximity to the transducer, is desirable. For instance, we have found a commercial preamplifier, Ithaco Model 143F, to be satisfactory. The signal is further amplified in amplifier 54, and then fed to boxcar integrator 55. As is well known, a boxcar allows the time gating of the signal portion to be integrated, thereby permitting the use of any particular small portion of a complicated signal. We found this feature to be very convenient, as will become clear later, but, of course, useful results could be obtained without it. The output of pyroelectric detector 56 is fed to a second boxcar integrator 57, and ratiometer 58 serves to form the ratio (A/B), that is, the ratio between the integrated OA signal and the integrated light pulse intensity. This ratio is then recorded by recorder 60 as a function of frequency $\nu$, and the resulting curve is the normalized absorption of the film 50 as a function of frequency.

Those skilled in the art will be easily able to modify the instrumentation scheme shown in FIG. 4 to fit particular requirements that may arise. For instance, it would be an obvious step to replace ratiometer 58 by a microprocessor or computer. Similarly, pulsed light source 51 does not have to be a pulsed dye laser. For instance, it could be a pulsed arc lamp, or even a continuously emitting light source together with a mechanical or electrooptical chopping device. In such a case, however, a spectrometer or other narrow-banding device would be required in order to select an appropriately narrow frequency band from the output of the light source. As an example of possible instrumentation, we have used a commercial scannable flash-lamp-pumped dye laser that produced about 1 mJ energy in about 1 $\mu$sec duration pulses, at a laser bandwidth of about 2 $cm^{-1}$. A useful repetition frequency is about 10 pulses per second, but of course a wide range of repetition rates can be used, as long as care is taken that the energy absorbed does not result in a significant steady-state rise in temperature of the sample layer. The bandwidth of the light used would depend on the desired spectral resolution, and could vary from perhaps 0.1 $cm^{-1}$ for some low temperature investigations to perhaps about 100 $cm^{-1}$ or more. One possible pyroelectric detector is a coated lithium niobate detector, such as, for instance, Laser Precision Model 2050S.

Figure 5:
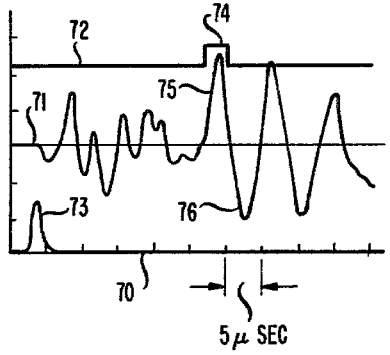
FIG. 5 shows oscilloscope traces of several relevant wave forms for the case of OA spectroscopy on a relatively absorptive layer.
Figure 6:
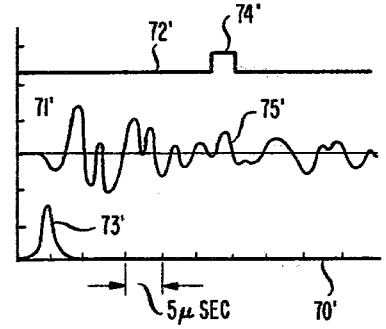
FIG. 6 shows the same oscilloscope traces for the case of a relatively transparent layer.

FIG. 5 shows a reproduction of three oscilloscope traces, trace 70 corresponding to the output of pyroelectric detector 56 of FIG. 4, trace 71 corresponding to the amplified output of transducer 16 of FIG. 4, and trace 72 showing the position and width of the gate of boxcar 55 from that figure. As can be seen, light pulse 73 has an approximate width of 13 $\mu$sec. Almost simultaneously with the occurrence of the light pulse the transducer begins to have a finite output that persists for some 20 $\mu$sec or more. This signal is due to scattered light effects and to "ringing" of the transducer. After a delay of some 25 $\mu$sec, corresponding to the travel time of compressional waves in the substrate, the true OA signal appears. As theory had predicted, the initial signal corresponds to a compression pulse 75, followed by rarefaction pulse 76. Later parts of the OA signal are due to transducer ringing. By properly positioning the boxcar gate, one can, for instance, look at the initial, i.e., compressional, OA pulse only, thereby avoiding all difficulties due to scattered light or ringing. The gate position 74 shown would accomplish this result. The trace 71 of FIG. 5 was obtained with a sample consisting of $Ho_2O_3$ particles suspended in a clear, viscous liquid, with the laser frequency tuned to an absorption line of the powder material. FIG. 6 shows the analogous trace for the case where the laser was tuned off any absorption line, that is, for the case where the suspension was essentially transparent. The numbering of FIG. 6 corresponds to that of the analogous features in FIG. 5. As can be seen, trace 71' consists essentially of signals due to scattered light and ringing, and only a very small OA pulse 75' is present.

Figure 7:
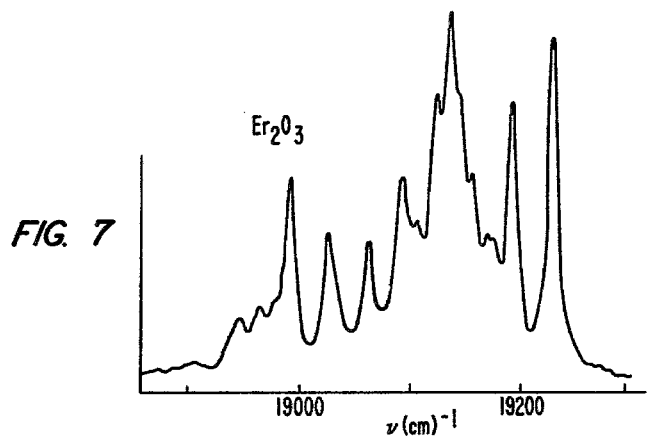
FIG. 7 shows actual data from the OA measurement of a thin layer consisting of a suspension of rare earth oxide particles in a transparent liquid.

In FIG. 7 we show results of an actual measurement of a rare earth oxide powder, in this case $Er_2O_3$, as obtained by OA spectroscopy at room temperature, in the manner indicated above. Without going into any interpretation of the observed absorption spectrum, we merely want to draw attention to the high sensitivity of our method, which clearly permits resolution of features only a few $cm^{-1}$ wide, and which is orders of magnitude better than that obtainable by prior art methods.

As we have already indicated above, our method is not only applicable to thin liquid films, to suspensions of absorbing solid particles in essentially transparent liquids, to continuous solid films as well as to discontinuous ones, and even to monolayers of strongly absorbing molecules, but also to layers of absorbing atoms or molecules inside an essentially transparent solid matrix. For instance, this permits OA spectroscopy of dopants in semiconductors, and thus is clearly of great interest in semiconductor research as well as semiconductor device processing. Another application of our method is to the study of surfaces. In particular, the sample layer can be a surface layer of the substrate that has become, due to some physical or chemical change in the surface layer, less transparent than is the bulk of the substrate material. In fact, many other applications for the here disclosed method for OA spectroscopy are possible, and will be found by those skilled in the art. Because of this breadth of our invention, we do not intend to limit its scope to the examples disclosed herein.

We claim:

1. A method for high-sensitivity optoacoustic spectroscopy of samples of condensed matter in layer form, comprising
    (a) selecting a solid substrate that consists at least in part of material essentially transparent to a probe radiation of frequency $\nu$, at least part of the substrate being adapted to permit propagation therein of ultrasonic waves having frequencies much larger than a repetition frequency $\nu$, the substrate containing a substrate source region, and, located to be nonoverlapping with that source region, a detection region, and the substrate source region being in intimate contact with at least part of the sample of condensed matter comprising a layer source region,
    (b) irradiating the substrate source region and the layer source region with intermittent probe radiation of frequency $\nu$, the repetition rate of the intermittent irradiation being $\nu_R$,
    (c) detecting ultrasonic waves of frequencies much greater than $\nu_R$ that arrive at the detection region of the substrate after propagation through at least part of the substrate, whereby the absorption of the probe radiation of frequency $\nu$ in the sample layer can be determined.

2. The method of claim 1 wherein the sample layer consists of a suspension of solid particles in a liquid that is essentially transparent to the probe radiation.

3. The method of claim 1 wherein the sample layer consists of at least one layerlike distribution of atoms or molecules of at least a first kind within an essentially transparent solid matrix consisting of atoms or molecules other than of the first kind.

4. The method of claim 1 wherein the sample layer consists at least of a part of at least one surface of the substrate, the part of the surface being less transparent to the probe radiation than the bulk of the substrate.

5. The method of claim 1 wherein the sample layer consists of a continuous liquid or solid film.

6. The method of claim 1 wherein the sample layer consists of a discontinuous solid layer.

7. The method of claim 1 wherein the peak amplitude of an electrical signal that is essentially proportional to the peak amplitude of the detected ultrasonic waves is recorded.

8. Apparatus for high-sensitivity optoacoustic spectroscopy of samples of condensed matter in layer form, comprising
(a) a solid substrate consisting at least in part of material essentially transparent to a probe radiation of frequency $\nu$, at least part of the substrate being adapted to permit propagation of ultrasonic waves having frequencies much larger than a repetition frequency $\nu_R$, the substrate containing a substrate source region and, located to be nonoverlapping with the source region, a detection region, at least the substrate source region adapted to support the sample of condensed matter,
(b) means for irradiating the substrate source region and the part of the sample in contact therewith with intermittent probe radiation of frequency $\nu$ at a repetition frequency $\nu_R$,
(c) means for detecting ultrasonic waves of frequencies much greater than the repetition frequency $\nu_R$ that arrive at the detection region of the substrate after propagation through at least part of the substrate.

9. Apparatus of claim 8 wherein the substrate consists at least in part of fused quartz.

10. Apparatus of claim 8 wherein the substrate is of a shape that does not permit the drawing of any straight line, lying entirely in the substrate surface, between source region and detection region.

11. Apparatus of claim 8 wherein the irradiation means comprise a pulsed laser.

12. Apparatus of claim 8 wherein the means for detecting ultrasonic waves comprise a piezoelectric bulk transducer.

13. Apparatus of claim 8 wherein the means for detecting ultrasonic waves comprise a surface acoustic wave transducer.

14. Apparatus of claims 12 or 13 further comprising means for measuring a part of an intermittent electrical signal by means of a time-gating technique.

* * * * *